US00PP29081P2

(12) United States Plant Patent
van Sambeek

(10) Patent No.: US PP29,081 P2
(45) Date of Patent: Mar. 6, 2018

(54) ***PENSTEMON* PLANT NAMED 'BARPENPEPPUR'**

(50) Latin Name: *Penstemon hartwegii*
Varietal Denomination: Barpenpeppur

(71) Applicant: Ellen van Sambeek, Aalsmeer (NL)

(72) Inventor: Ellen van Sambeek, Aalsmeer (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/330,232

(22) Filed: Aug. 27, 2016

(51) Int. Cl.
*A01H 5/02* (2006.01)

(52) U.S. Cl.
USPC ..... Plt./465

(58) Field of Classification Search
USPC ..... Plt./465
See application file for complete search history.

*Primary Examiner* — Anne M Grunberg
(74) *Attorney, Agent, or Firm* — C. A. Whealy

(57) ABSTRACT

A new and distinct cultivar of *Penstemon* plant named 'Barpenpeppur', characterized by its upright and relatively compact plant habit; vigorous growth habit; freely branching habit; early and freely flowering habit; long flowering period; dark red purple-colored flowers with light pink-colored centers; and good garden performance.

1 Drawing Sheet

Botanical designation: *Penstemon hartwegii.*
Cultivar denomination: 'BARPENPEPPUR'.

CROSS-REFERENCED TO CLOSELY-RELATED APPLICATIONS

Title: *Penstemon* Plant Named 'BARPENPEPPIN'
Applicant: Ellen van Sambeek
Filed: Concurrently with this application having application Ser. No. 15/330,230.

BACKGROUND OF THE INVENTION

The present invention relates to a new and distinct cultivar of *Penstemon* plant, botanically known as *Penstemon hartwegii* and hereinafter referred to by the name 'Barpenpeppur'.

The new *Penstemon* plant is a product of a planned breeding program conducted by the Inventor in Aalsmeer, The Netherlands. The objective of the breeding program was to create new early-flowering *Penstemon* plants with attractive flower color.

The new *Penstemon* plant originated from a cross-pollination made by the Inventor in August, 2013 in Aalsmeer, The Netherlands, of a proprietary selection of *Penstemon hartwegii* identified as code number Pe-0003, not patented, as the female, or seed, parent with a proprietary selection of *Penstemon hartwegii* identified as code number Pe-0099, not patented, as the male, or pollen, parent. The new *Penstemon* plant was discovered and selected by the Inventor as a single flowering plant from within the progeny of the stated cross-pollination in a controlled environment in Aalsmeer, The Netherlands in April, 2014.

Asexual reproduction of the new *Penstemon* plant by cuttings in a controlled environment in Aalsmeer, The Netherlands since April, 2014 has shown that the unique features of this new *Penstemon* plant are stable and reproduced true to type in successive generations.

SUMMARY OF THE INVENTION

Plants of the new *Penstemon* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Barpenpeppur'. These characteristics in combination distinguish 'Barpenpeppur' as a new and distinct *Penstemon* plant:

1. Upright and relatively compact plant habit.
2. Vigorous growth habit.
3. Freely branching habit.
4. Early and freely flowering habit.
5. Long flowering period.
6. Dark red purple-colored flowers with light pink-colored centers.
7. Good garden performance.

Plants of the new *Penstemon* differ primarily from plants of the female parent selection in the following characteristics:

1. Plants of the new *Penstemon* are more compact than plants of the female parent selection.
2. Plants of the new *Penstemon* flower earlier than plants of the female parent selection.

Plants of the new *Penstemon* differ primarily from plants of the male parent selection in the following characteristics:

1. Plants of the new *Penstemon* are more compact than plants of the male parent selection.
2. Plants of the new *Penstemon* are more freely flowering than plants of the male parent selection.
3. Plants of the new *Penstemon* and the male parent selection differ in flower color as plants of the male parent selection have solid red-colored flowers.

Plants of the new *Penstemon* can be compared to plants of *Penstemon hartwegii* 'Barpenpeppin', disclosed in a U.S. Plant Patent application filed concurrently. Plants of the new *Penstemon* and 'Barpenpeppin' differ primarily in flower color as plants of 'Barpenpeppin' have lighter red purple-colored flowers with light pink-colored centers. In addition, plants of the new *Penstemon* are more compact than plants of 'Barpenpeppin'.

Plants of the new *Penstemon* can also be compared to plants of *Penstemon hartwegii* 'Polaris Purple', not patented. In side-by-side comparisons, plants of the new *Penstemon* and 'Polaris Purple' differ in the following characteristics:

1. Plants of the new *Penstemon* are more compact than plants of 'Polaris Purple'.
2. Plants of the new *Penstemon* have longer leaves than plants of 'Polaris Purple'.
3. Plants of the new *Penstemon* flower earlier than plants of 'Polaris Purple'.
4. Plants of the new *Penstemon* are more freely flowering than plants of 'Polaris Purple'.

BRIEF DESCRIPTION OF THE PHOTOGRAPH

The accompanying colored photograph illustrates the overall appearance of the new *Penstemon* plant showing the colors as true as it is reasonably possible to obtain in colored reproductions of this type. Colors in the photograph may differ slightly from the color values cited in the detailed botanical description which accurately describe the colors of the new *Penstemon* plant.

The photograph comprises a side perspective view of typical flowering plant of 'Barpenpeppur' grown in a container.

DETAILED BOTANICAL DESCRIPTION

The aforementioned photograph and following observations, measurements and values describe plants grown during the summer in 13-cm containers in an outdoor nursery in Aalsmeer, The Netherlands and under cultural practices typical of commercial *Penstemon* production. During the production of the plants, day temperatures averaged 22° C. and night temperatures averaged 17° C. Plants were pinched one time and were three months old when the photograph was taken and six months old when the description was taken. In the following description, color references are made to The Royal Horticultural Society Colour Chart, 2001 Edition, except where general terms of ordinary dictionary significance are used.

Botanical classification: *Penstemon hartwegii* 'Barpenpeppur'.

Parentage:

*Female, or seed, parent.*—Proprietary selection of *Penstemon hartwegii* identified as code number Pe-0003, not patented.

*Male, or pollen, parent.*—Proprietary selection of *Penstemon hartwegii* identified as code number Pe-0099, not patented.

Propagation:

*Type.*—By vegetative cuttings.

*Time to initiate roots, summer.*—About 12 days at temperatures about 26° C.

*Time to initiate roots, winter.*—About 16 days at temperatures about 23° C.

*Time to produce a rooted young plant, summer.*—About 16 days at temperatures about 23° C.

*Time to produce a rooted young plant, winter.*—About 20 days at temperatures about 18° C.

*Root description.*—Medium in thickness, fibrous; typically white to light yellow in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Herbaceous perennial typically grown as a container and garden plant; upright and relatively compact plant habit; vigorous growth habit.

*Plant height.*—About 32 cm.

*Plant width (spread).*—About 30 cm.

*Lateral branches.*—Length: About 30 cm. Internode length: About 3 cm. Strength: Strong. Aspect: Upright. Texture: Pubescent. Color: Close to 145B.

Leaf description:

*Arrangement.*—Opposite, simple; sessile.

*Length.*—About 12 cm.

*Width.*—About 3.5 mm.

*Shape.*—Lanceolate.

*Apex.*—Acute.

*Base.*—Attenuate.

*Margin.*—Entire; towards the apex, dentate.

*Texture, upper and lower surfaces.*—Smooth, glabrous.

*Venation pattern.*—Pinnate, reticulate.

*Color.*—Developing leaves, upper surface: Close to 137B. Developing leaves, lower surface: Close to 137C. Fully expanded leaves, upper and lower surfaces: Close to 137C; venation, close to 145C.

Flower description:

*Flower shape, arrangement and flowering habit.*—Single bi-labiate flowers arranged on terminal racemes; flowers face mostly outwardly; freely flowering with about 45 flowers developing per inflorescence and about 240 flowers development per plant during the flowering season.

*Fragrance.*—None detected.

*Time to flower.*—Early flowering habit, plants begin to flower about eight to ten weeks after planting.

*Natural flowering season.*—Long flowering period, plants flower during the summer in The Netherlands; flowers not persistent.

*Flower buds.*—Length: About 1.5 cm. Diameter: About 8 mm. Shape: Ovoid. Color: Close to 71A.

*Inflorescence height.*—About 30 cm.

*Inflorescence diameter.*—About 9 cm.

*Flower diameter.*—About 3.5 cm.

*Flower depth (height).*—About 4 cm.

*Flower throat diameter.*—About 2 cm.

*Flower tube length.*—About 3 cm.

*Flower tube diameter, at base.*—About 6 mm.

*Petals.*—Arrangement: Five, fused into a tube; bilabiate, upper lip with two upper petals and lower lip with three lower petals. Length, upper and lower lips: About 4 mm. Width, upper lip: About 1.3 cm. Width, lower lip: About 1.6 cm. Shape: Rounded. Apex: Obtuse. Margin: Entire; slightly undulate. Texture, upper surface: Smooth, glabrous. Texture, lower surface: Pubescent. Texture, throat: Smooth, glabrous. Texture, tube: Pubescent. Color: When opening and fully opened, upper surface: Close to 71A; venation, close to 71A. When opening and fully opened, lower surface: Close to 71A; venation, close to 71A. Throat: Close to 69D; venation, close to 69D. Tube: Close to 71A; towards the base, close to 155A; venation, close to 71A.

*Sepals*.—Arrangement: Five sepals fused in a single whorl. Length: About 7 mm. Width: About 6 mm. Shape: Deltoid. Apex: Acute. Margin: Entire. Texture, upper surface: Smooth, glabrous. Texture, lower surface: Pubescent. Color: Developing and fully developed, upper surface: Close to 144D; towards the apex, close to 144A. Developing and fully developed, lower surface: Close to 144D; towards the apex, close to 144A.

*Peduncles*.—Length: About 28 cm. Diameter: About 6 mm. Aspect: Upright to about 30° from vertical. Strength: Strong. Texture: Smooth, glabrous. Color: Close to 145B.

*Pedicels*.—Length: About 1 cm. Diameter: About 2 mm. Aspect: About 25° from the peduncle axis. Strength: Strong. Texture: Pubescent. Color: Close to 146D.

*Reproductive organs*.—Stamens: Quantity per flower: Five. Filament length: About 2 cm to 2.7 cm. Filament color: Close to 155D. Anther length: About 3 mm. Anther color: Close to 165A. Pollen amount: Moderate. Pollen color: Close to 158A. Pistils: Quantity per flower: One. Pistil length: About 2.5 cm. Stigma shape: Rounded. Stigma color: Close to 155A. Style length: About 2 cm. Style color: Close to 70A; distally, close to 155B. Ovary color: Close to 145A.

*Seeds and fruits*.—Seed and fruit development have not been observed on plants of the new *Penstemon*.

Garden performance: Plants of the new *Penstemon* have been observed to have good garden performance and tolerate rain, wind and frost.

Disease & pest resistance: Plants of the new *Penstemon* have not been observed to be resistant to pathogens and pests common to *Penstemon* plants.

It is claimed:

1. A new and distinct *Penstemon* plant named 'Barpenpeppur' as illustrated and described.

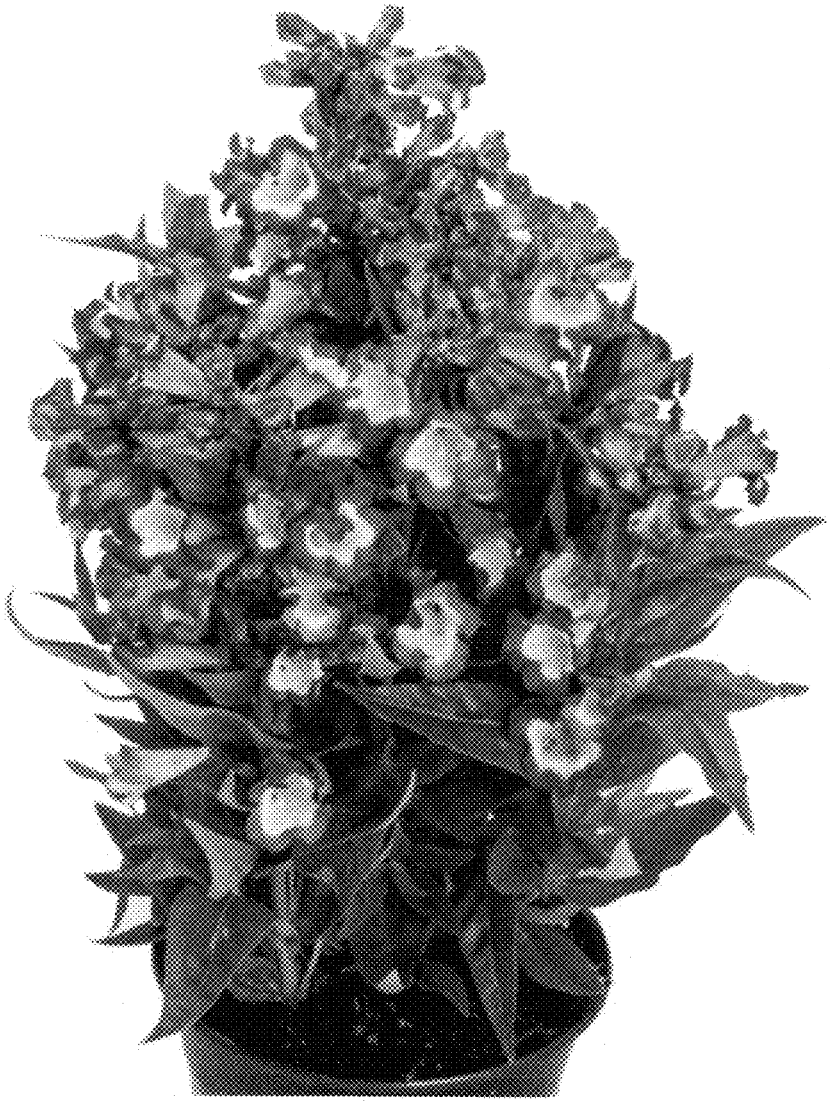

* * * * *